(12) United States Patent
Meyer et al.

(10) Patent No.: US 9,566,447 B2
(45) Date of Patent: Feb. 14, 2017

(54) NEURAL STIMULATION SYSTEM FOR REDUCING ATRIAL PROARRHYTHMIA

(75) Inventors: Scott A. Meyer, Lakeville, MN (US); Alok S. Sathaye, Minneapolis, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 2414 days.

(21) Appl. No.: 11/320,173

(22) Filed: Dec. 28, 2005

(65) Prior Publication Data

US 2007/0150011 A1  Jun. 28, 2007

(51) Int. Cl.
 *A61N 1/00* (2006.01)
 *A61N 1/37* (2006.01)
 *A61N 1/36* (2006.01)
 A61N 1/362 (2006.01)

(52) U.S. Cl.
 CPC ......... *A61N 1/3702* (2013.01); *A61N 1/36114* (2013.01); *A61N 1/3624* (2013.01)

(58) Field of Classification Search
 CPC . A61N 1/36114; A61N 1/3624; A61N 1/3702
 USPC ...................................... 607/9, 14
 See application file for complete search history.

(56) References Cited

U.S. PATENT DOCUMENTS

| 5,203,326 | A | 4/1993 | Collins |
| 5,356,425 | A | 10/1994 | Bardy et al. |
| 5,700,282 | A | 12/1997 | Zabara |
| 5,916,239 | A | 6/1999 | Geddes et al. |

(Continued)

FOREIGN PATENT DOCUMENTS

| EP | 1304135 | 4/2003 |
| EP | 1304135 A2 | 4/2003 |

(Continued)

OTHER PUBLICATIONS 06 83 7822.3, Application Serial No. 06 83 7822.3 Office Action Mailed Nov. 13, 2008, 5 pgs.

(Continued)

*Primary Examiner* — Niketa Patel
*Assistant Examiner* — Lindsey G Hankins
(74) *Attorney, Agent, or Firm* — Schwegman Lundberg & Woessner, P.A.

(57) ABSTRACT

A system for reducing proarrhythmic effects of neural stimulation is provided. One aspect of this disclosure relates to an implantable medical device (IMD) for reducing proarrhythmic effects of neural stimulation. The IMD includes a neural stimulator adapted to deliver an electrical signal through at least one electrode to provide vagal stimulation. The IMD also includes a controller adapted to receive atrial arrhythmia vulnerability data and to control a therapeutic stimulator to limit atrial proarrhythmia using the atrial arrhythmia vulnerability data. The controller is further adapted to receive atrial arrhythmic history data and to control a therapeutic stimulator to limit atrial proarrhythmia using the atrial arrhythmic history data, according to various embodiments. According to one embodiment, the therapeutic stimulator includes the neural stimulator. The therapeutic stimulator includes a cardiac stimulator adapted to provide cardiac rhythm management therapy, according to various embodiments. Other aspects and embodiments are provided herein.

30 Claims, 4 Drawing Sheets

(56) References Cited

U.S. PATENT DOCUMENTS

| | | | |
|---|---|---|---|
| 6,292,625 | B1 | 9/2001 | Gotoh et al. |
| 6,511,500 | B1* | 1/2003 | Rahme .............................. 607/1 |
| 6,690,971 | B2 | 2/2004 | Schauerte et al. |
| 2003/0009198 | A1* | 1/2003 | Boute ............................ 607/14 |
| 2003/0078623 | A1* | 4/2003 | Weinberg et al. ................ 607/9 |
| 2003/0100925 | A1 | 5/2003 | Pape et al. |
| 2003/0195574 | A1* | 10/2003 | Osorio et al. ..................... 607/9 |
| 2005/0075701 | A1 | 4/2005 | Shafer |
| 2005/0081847 | A1 | 4/2005 | Lee et al. |
| 2005/0149126 | A1 | 7/2005 | Libbus |
| 2005/0245975 | A1* | 11/2005 | Hettrick et al. .................. 607/9 |
| 2006/0253157 | A1 | 11/2006 | Libbus et al. |

FOREIGN PATENT DOCUMENTS

| | | |
|---|---|---|
| WO | WO-9910043 A1 | 3/1999 |
| WO | WO-03041559 A2 | 5/2003 |
| WO | WO-2005035056 A1 | 4/2005 |
| WO | WO-2007075232 A1 | 7/2007 |

OTHER PUBLICATIONS

International Search Report for Application No. PCT/US2006/044560, (Mar. 23, 2007),13.

Alessi, R. , "Nonuniform distribution of vagal effects on the atrial refractory period", *Am J Physiol*, 194(2), (Aug. 1958),406-10.

Ali, I. M., "Modification of supraventricular tachyarrhythmias by stimulating atrial neurons", *Ann Thorac Surg*, 50(2), (Aug. 1990),251-6.

Armour, J. A., et al., "Origin and pharmacological response of atrial tachyarrhythmias induced by activation of mediastinal nerves in canines", *Autonomic Neuroscience*, 118(1-2), (Mar. 31, 2005),68-78.

Coumel, P. , "Paroxysmal atrial fibrillation a disorder of autonomic tone?", *Eur Heart J 15 Suppl A*, (Apr. 1994),9-16.

Coumel, P. , "The atrial arrhythmia syndrome of vagal origin", *Archives des Maladies du Coeur et des Vaisseaux.*, 71(6), French,(Jun. 1978),645-56.

Liu, L. , "Differing sympathetic and vagal effects on atrial fibrillation in dogs role of refractoriness heterogeneity", *Am J Physiol*, 273(2 Pt 2), (Aug. 1997),H805-16.

Page, P. L., "Regional distribution of atrial electrical changes induced by stimulation of extracardiac and intracardiac neural elements", *J Thorac Cardiovasc Surg*,109(2), (Feb. 1995),377-88.

Zipes, D. P., "Effects of selective vagal and stellate ganglion stimulation of atrial refractoriness", *Cardiovasc Res*, 8(5), (Sep. 1974),647-55.

European Application Serial No. 06837822.3, Summons to Attend Oral Proceeding mailed Aug. 19, 2010, 7 pgs.

European Application Serial No. 06837822.3, Summons to attend Oral Proceeding mailed Sep. 22, 2010, 1 pg.

European Application Serial No. 10190170.0,Extended European Search Report mailed Apr. 19, 2011, 9 pgs.

\* cited by examiner

NEURAL STIMULATION SYSTEM FOR REDUCING ATRIAL PROARRHYTHMIA

TECHNICAL FIELD

This disclosure relates generally to implantable medical devices and, more particularly, to systems and methods of reducing atrial proarrhythmia from neural stimulation.

BACKGROUND

The autonomic system controls physiological activities of the body and the imbalance of autonomic tone (sympathetic/parasympathetic balance) is related to many diseases and conditions, including sleep disorders, eating disorders, obesity, anorexia, gastrointestinal tract disorders, hypertension, coma and epilepsy. Increased sympathetic and decreased parasympathetic tone during heart failure have been shown to be associated with left ventricular dysfunction and increased mortality. Conversely, sympathetic inhibition, as well as parasympathetic activation, have been associated with reduced arrhythmia vulnerability following a myocardial infarction and are thought to be cardioprotective in nature. Direct electrical stimulation of parasympathetic nerves can activate the baroreflex, inducing a reduction of sympathetic nerve activity and reducing blood pressure by decreasing vascular resistance. Moreover, direct stimulation of the vagal parasympathetic fibers has been shown to reduce heart rate. In addition, some research indicates that chronic stimulation of the vagus nerve may be of protective myocardial benefit following cardiac ischemic insult.

Neural stimulation therapy, such as cardioprotective vagal stimulation following myocardial infarction (MI) has the potential to produce proarrhythmic effects. Vagal stimulation may shorten atrial effective refractory period (AERP) and increase dispersion of refractoriness, thereby increasing vulnerability to atrial fibrillation. Vulnerability to atrial fibrillation may be increased in patients with prior MI or dialted cardiomyopathy with mitral regurgitation, since stretching of atrial tissue may increase ectopy.

SUMMARY disclosed herein, among other things, is an implantable medical device (IMD) for monitoring and/or reducing proarrhythmic effects of neural stimulation. The IMD includes a neural stimulator adapted to deliver an electrical signal through at least one electrode pair to provide vagal stimulation. The MD also includes a controller adapted to receive atrial arrhythmia vulnerability and/or atrial arrhythmic history data and to control a therapeutic stimulator to limit atrial proarrhythmia using the atrial arrhythmia vulnerability and/or atrial arrhythmic history data. According to one embodiment, the therapeutic stimulator includes the neural stimulator. The therapeutic stimulator may also include a cardiac stimulator adapted to provide cardiac rhythm management therapy, according to various embodiments.

Another aspect of the device includes both a neural stimulator and an atrial stimulator. The neural stimulator is adapted to deliver an electrical signal through at least one electrode pair to provide vagal stimulation, and the atrial stimulator is adapted to deliver an electrical signal through at least one electrode pair to provide cardiac rhythm management therapy. The device also includes a controller adapted to receive atrial arrhythmia vulnerability data and/or atrial arrhythmia history data, and to control the neural stimulator and the atrial stimulator to limit atrial proarrhythmia using the atrial arrhythmia vulnerability data and/or atrial arrhythmia history data. According to various embodiments, the device includes a sensing circuit adapted to be connected to at least one sensor, the at least one sensor adapted to monitor atrial activity to measure atrial arrhythmia vulnerability.

One aspect of this disclosure relates to a system for titrating neural stimulation therapy to reduce proarrhythmic effects of vagal stimulation. The system includes at least one neural stimulation lead having a proximal portion and a distal portion. The system also includes a plurality of electrodes along the distal portion of the at least one lead, and an IMD coupled to the proximal portion of the at least one lead. The IMD includes a neural stimulator adapted to deliver an electrical signal through at least one electrode pair to provide vagal stimulation. The IMD also includes a controller adapted to receive atrial arrhythmia vulnerability data and to control the neural stimulator to limit atrial proarrhythmia using the atrial arrhythmia vulnerability data.

Another aspect of the system includes an implanted neural stimulator adapted to deliver an electrical signal through at least one electrode pair to provide vagal stimulation. The system also includes an external monitoring device wirelessly coupled to the stimulator. According to various embodiments, the external device includes a monitoring module adapted to monitor atrial activity to measure atrial vulnerability and to record an historical arrhythmic profile. The external device also includes a controller module adapted to receive atrial arrhythmia vulnerability data and to control the neural stimulator to limit atrial proarrhythmia using the atrial arrhythmia vulnerability data, according to an embodiment.

One aspect of this disclosure relates to a method of titrating neural stimulation therapy to reduce proarrhythmic effects of neural stimulation. The method includes applying neural stimulation therapy to deliver vagal stimulation. The method also includes monitoring atrial activity or electrophysiologic parameters to detect changes related to the application of neural stimulation therapy. The method further includes titrating the applied therapy to limit atrial proarrhythmia in response to the detected changes in atrial activity or atrial electrophysiologic measurements.

Another aspect of this disclosure relates to a method of applying atrial stimulation therapy to reduce proarrhythmic effects of neural stimulation. The method includes applying neural stimulation therapy to deliver cardioprotective vagal stimulation. The method also includes applying cardiac rhythm management strategies for preventing atrial arrhythmia. According to various embodiments, the method further includes monitoring atrial activity to detect changes related to the application of neural stimulation therapy, and applying cardiac rhythm management strategies for preventing atrial arrhythmia in response to the detected changes in atrial activity.

This Summary is an overview of some of the teachings of the present application and is not intended to be an exclusive or exhaustive treatment of the present subject matter. Further details are found in the detailed description and appended claims. Other aspects will be apparent to persons skilled in the art upon reading and understanding the following detailed description and viewing the drawings that form a part thereof, each of which is not to be taken in a limiting sense. The scope of the present invention is defined by the appended claims and their legal equivalents.

DETAILED DESCRIPTION

Figure 1A:
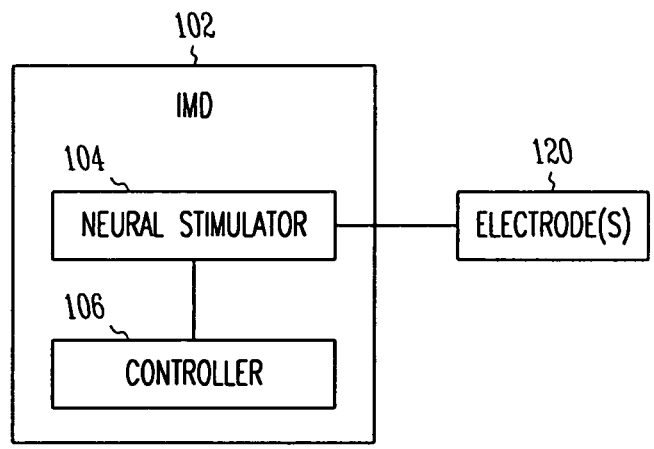
FIG. 1A illustrates an implantable medical device (IMD) for reducing proarrhythmic effects of neural stimulation, according to one embodiment.

The following detailed description refers to the accompanying drawings which show, by way of illustration, specific aspects and embodiments in which the present invention may be practiced. These embodiments are described in sufficient detail to enable those skilled in the art to practice the invention. Other embodiments may be utilized and structural, logical, and electrical changes may be made without departing from the scope of the present invention.
Neural Stimulation A brief discussion of the physiology related to neurology is provided to assist the reader with understanding this disclosure. The automatic nervous system (ANS) regulates "involuntary" organs. The ANS includes the sympathetic nervous system and the parasympathetic nervous system. The sympathetic nervous system is affiliated with stress and the "fight or flight response" to emergencies. The parasympathetic nervous system is affiliated with relaxation and the "rest and digest response." The ANS maintains normal internal function and works with the somatic nervous system. Autonomic balance reflects the relationship between parasympathetic and sympathetic activity. A change in autonomic balance is reflected in changes in heart rate, heart rhythm, contractility, remodeling, inflammation and blood pressure. Changes in autonomic balance can also be seen in other physiological changes, such as changes in abdominal pain, appetite, stamina, emotions, personality, muscle tone, sleep, and allergies, for example.

Stimulation of a vagus nerve trunk is used in a number of therapies. Increased sympathetic nervous activity following ischemia often results in increased exposure of the myocardium to epinephrine and norepinephrine. These catecholamines activate intracellular pathways within the myocytes, which lead to myocardial death and fibrosis. This effect is inhibited by stimulation of the parasympathetic nerves, such as vagus nerves. Vagal stimulation has been shown to lower heart rate, overall blood pressure, and left ventricular pressure, as well as simultaneously increasing parasympathetic and tone decreasing sympathetic tone. Stimulation of the vagal cardiac nerves following myocardial infarction, or in heart failure patients, can be beneficial in preventing further remodeling and arrhythmogenesis.

An example of neural stimulation is baroreflex stimulation. Baroreflex is a reflex triggered by stimulation of a baroreceptor. A baroreceptor includes any sensor of pressure changes, such as sensory nerve endings in the wall of the auricles of the heart, vena cava, aortic arch and carotid sinus, that is sensitive to stretching of the wall resulting from increased pressure from within, and that functions as the receptor of the central reflex mechanism that tends to reduce that pressure. Afferent nerve trunks, such as the vagus, aortic and carotid nerves, leading from the sensory nerve endings also form part of a baroreflex pathway. Stimulating a baroreflex pathway and/or baroreceptors inhibits sympathetic nerve activity, stimulates the parasympathetic nervous system and reduces systemic arterial pressure by decreasing peripheral vascular resistance and cardiac contractility. Baroreceptors are naturally stimulated by internal pressure and the stretching of vessel wall (e.g. arterial wall). Neural stimulation of other neural targets is within the scope of the present disclosure, including stimulation of efferent and afferent pathways for parasympathetic and sympathetic nerves.

A neural stimulation lead is a lead for delivering neural stimulation therapy, and can be placed in a number of appropriate locations. For example, various lead embodiments to stimulate a baroreflex are expandable, and are adapted to be placed in an artery in the proximity of a high concentration of baroreceptors. Various lead embodiments are adapted to stimulate nerve endings in cardiac fat pads. Some lead embodiments are transvascular leads placed proximal to a cardiac fat pad. Some lead embodiments place an epicardial lead in a cardiac fat pad. Various lead embodiments include a cuff electrode adapted to be placed around a nerve, such as the aortic, carotid or vagus nerve. A nerve cuff refers to any lead configuration that is placed around a nerve trunk, including configurations placed around a sheath containing a nerve trunk. Some lead embodiments include a transvascular lead placed proximal to a nerve, such as the vagus, aortic, or carotid nerve. Other leads can be placed in other neural stimulation and neural sensing locations to perform baroreflex or other therapy.
Proarrhythmic Effects of Neural Stimulation Vagal stimulation may shorten atrial effective refractory period (AERP) and increase dispersion of refractoriness, thereby increasing vulnerability to atrial fibrillation. Vulnerability to atrial fibrillation may be increased in patients with prior myocardial infarction (MI) or dilated cardiomyopathy with mitral regurgitation, since stretch of atrial tissue may increase ectopy. Neural stimulation therapy, such as cardioprotective vagal stimulation following MI, therefore has the potential to produce proarrhythmic side effects.

Proarrhythmic side effects can be manifested as signs or symptoms of increased atrial arrhythmia vulnerability. Atrial arrhythmia vulnerability data includes changes in atrial arrhythmia frequency, duration, etiology or relative timing related to the introductory or delivery of neural stimulation therapy. Additional signs of atrial arrhythmia vulnerability include an increase in premature atrial complexes (PACs), PAC trains, or atrial flutter. PACs are abnormal electrical impulses arising in the atria.

Additional indicia of proarrhythmic effects can be observed by making active measurements of atrial electrophysiology parameters, such as evoked response and monophasic action potentials (MAPs), which are signals by which unipolar electrogram areas and AERP can be measured. What are needed are enhanced strategies for counteracting the potential proarrhythmic effects of cardiac neural stimulation.

This disclosure provides for the reduction of the negative side effects of neural stimulation (such as proarrhythmic effects) via adaptive delivery of neural stimulation or pacing therapy. The present system provides an implantable medical device (IMD) for applying neural stimulation therapy, such as cardioprotective vagal stimulation following MI. In various embodiments, the system reduces the proarrhythmic effects of neural stimulation by titrating, or reducing, the neural stimulation delivery using available atrial arrhythmia vulnerability data and/or atrial arrhythmic history data (such as atrial arrhythmic episode trends). The system reduces the proarrhythmic effects of neural stimulation by applying active pacing pulses, in various embodiments.

Implantable Medical Devices

FIG. 1A illustrates an implantable medical device (IMD) for reducing proarrhythmic effects of neural stimulation, according to one embodiment. The IMD 102 includes a neural stimulator 104 adapted to deliver an electrical signal through at least one electrode pair 120 to provide vagal stimulation, including cardioprotective vagal stimulation in an embodiment. The IMD 102 also includes a controller 106 adapted to receive atrial arrhythmia vulnerability data and/or atrial arrhythmic history data, and to control a therapeutic stimulator to limit atrial proarrhythmia using the atrial arrhythmia vulnerability data and/or atrial arrhythmic history data. According to the depicted embodiment, the therapeutic stimulator includes the neural stimulator 104. The therapeutic stimulator includes a cardiac stimulator (such as a pacemaker, pulse generator or other implantable cardiac device) adapted to provide cardiac rhythm management therapy, according to various embodiments. While the neural stimulator 104 is shown physically coupled to the at least one electrode pair 120, the neural stimulator can be wirelessly coupled to the at least one electrode pair in various embodiments. Thus, leadless stimulation may be applied through wireless communication, such as ultrasound or radio frequency, from neural stimulator to electrode or from therapeutic stimulator to electrode.

The controller 106 is adapted to control the neural stimulator to limit therapy delivery to a specific time period related to atrial arrhythmic risk, according to various embodiments. In one embodiment, the controller is adapted to control the neural stimulator to deliver therapy only when a patient is awake. In another embodiment, the controller is adapted to control the neural stimulator to deliver therapy only when a patient is asleep.

According to various embodiments, the controller 106 is adapted to control the neural stimulator to reduce therapy delivery when one or more indicators of arrhythmic vulnerability are present. The indicators of arrhythmic vulnerability may include an increase in premature atrial complexes (PACs), an increase in PAC trains, an increase in atrial flutter, or an increase in premature ventricular complexes (PVCs) in various embodiments. According to various embodiments the controller is adapted to control the neural stimulator to reduce therapy delivery based on atrial arrhythmic history data.

According to various embodiments, the device includes means for delivering an electrical signal to provide vagal stimulation, and further includes means for controlling a therapeutic stimulator to limit atrial proarrhythmia using atrial arrhythmia vulnerability data. The delivering means includes a neural stimulator and the controlling means includes a controller, such as a microprocessor, according to various embodiments. Other embodiments are within the scope of this disclosure.

Figure 1B:
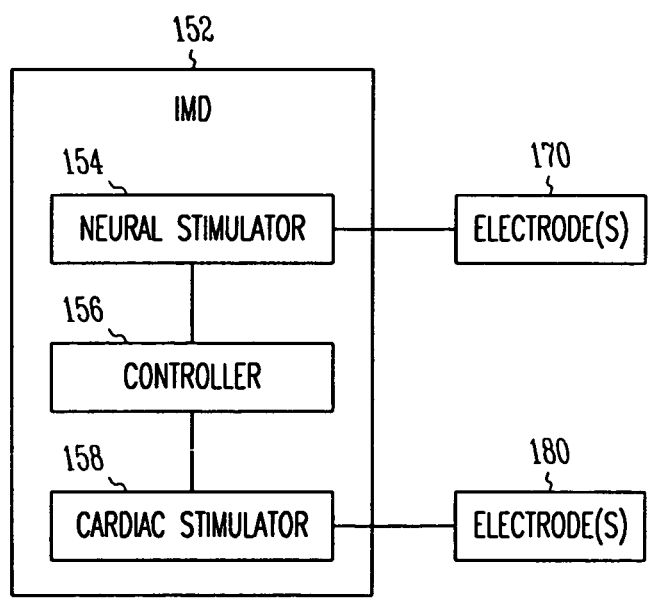
FIG. 1B illustrates an IMD for reducing proarrhythmic effects of neural stimulation including a cardiac stimulator, according to one embodiment.

FIG. 1B illustrates an IMD for reducing proarrhythmic effects of neural stimulation including a cardiac stimulator, according to one embodiment. The IMD 152 includes neural stimulator 154 which is adapted to deliver an electrical signal through at least one electrode pair 170 to provide vagal stimulation, including cardioprotective vagal stimulation in an embodiment. The IMD 152 also includes a cardiac stimulator 158 which is adapted to deliver an electrical signal through at least one electrode pair 180 to provide cardiac rhythm management therapy. The IMD 152 further includes a controller 156 adapted to receive atrial arrhythmia vulnerability data and/or atrial arrhythmic history data and to control the neural stimulator 154 and the cardiac stimulator 158 to limit atrial proarrhythmia using the atrial arrhythmia vulnerability data and/or atrial arrhythmic history data. In one embodiment, the neural and cardiac stimulators are in separate IMDs. The neural and cardiac stimulators may use the same or different electrodes, and may be wirelessly or directly connected to the electrodes.

The depicted device can be used to deliver neural stimulation in conjunction with active cardiac rhythm management strategies for preventing atrial arrhythmia. According to one embodiment, algorithms for preventing paroxysmal atrial fibrillation, such as overdrive pacing or multi-site atrial) pacing are automatically engaged during delivery of neural stimulation. The device activates anti-arrhythmia algorithms in response to detected atrial events, according to an embodiment.

According to various embodiments, the device includes at least one sensor adapted to monitor atrial activity to measure atrial arrhythmia vulnerability. The controller 156 is adapted to receive atrial arrhythmia vulnerability data from a sensor, according to various embodiments. According to various embodiments, the controller is adapted to access pre-recorded atrial arrhythmia vulnerability data. For example, in one embodiment the controller is adapted to access pre-recorded atrial arrhythmia vulnerability data from a logbook. Another example includes an embodiment where the controller is adapted to access pre-recorded atrial arrhythmia vulnerability data from a database. According to various embodiments, the controller is adapted to access atrial arrhythmic history data from a memory within the implantable medical device.

System for Reducing Proarrhythmic Effects of Neural Stimulation

Figure 2:
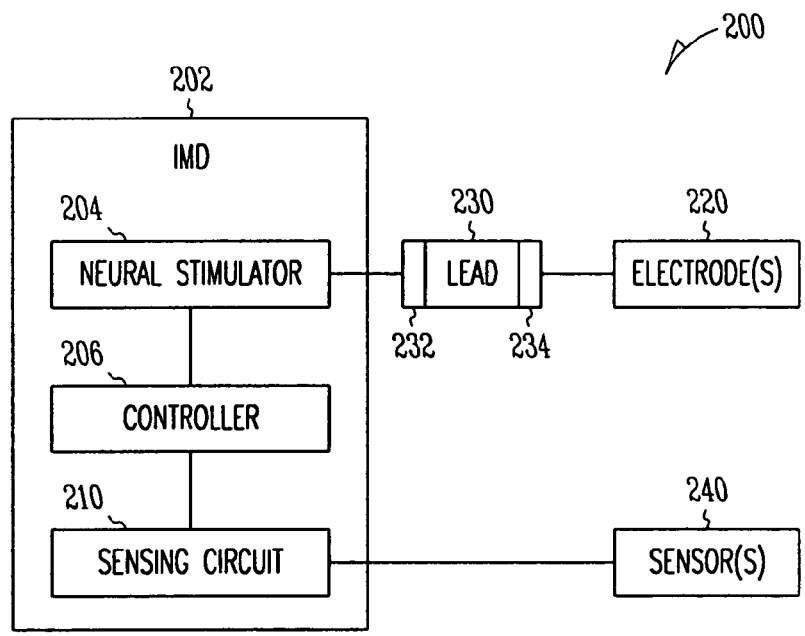
FIG. 2 illustrates an implantable system for reducing proarrhythmic effects of neural stimulation including a sensing circuit, according to one embodiment.

FIG. 2 illustrates an implantable system for reducing proarrhythmic effects of neural stimulation including a sensing circuit, according to one embodiment. The system 200 includes at least one neural stimulation lead 230 having a proximal portion 232 and a distal portion 234. The system 200 also includes a plurality of electrodes 220 along the distal portion 234 of the lead 230, and an IMD 202 coupled to the proximal portion 232 of the lead 230. The IMD 202 includes a neural stimulator 204 adapted to deliver an electrical signal through at least one electrode pair 220 to provide vagal stimulation, including cardioprotective vagal stimulation in an embodiment. The IMD 202 also includes a sensing circuit 210 adapted to be connected to at least one sensor 240, the at least one sensor adapted to monitor atrial activity to measure atrial arrhythmia vulnerability. The IMD 202 further includes a controller 206 adapted to receive measured data from the sensing circuit 210 and to control the neural stimulator 204 to limit atrial proarrhythmia using the measured data. According to various embodiments, the IMD includes a cardiac rhythm management device, such as a pacemaker or other implantable cardiac device.

According to various embodiments, at least one sensor 240 is adapted to actively measure atrial electrophysiology parameters. The controller is then adapted to control the neural stimulator to limit atrial proarrhythmia based on the atrial electrophysiology parameters. Examples of sensed atrial electrophysiology parameters include an evoked response, unipolar electrogram areas, monophasic action potentials (MAPs), or atrial effective refractory periods (AERP) in various embodiments. According to various embodiments, the controller is further adapted to receive atrial arrhythmic history data and to control the neural stimulator to limit atrial proarrhythmia using the atrial arrhythmic history data.

Various types of leads may be used in conjunction with the neural stimulator 204. For example, the lead 230 may include a lead with an expandable portion, a transvascular lead (placed proximal to the vagus nerve, for example), or an epicardial lead. Various types of electrodes may also be used. For example, a cuff electrode may be placed around the vagus nerve. As those skilled in the art are aware, additional electrode and lead types may be used.

Figure 3:
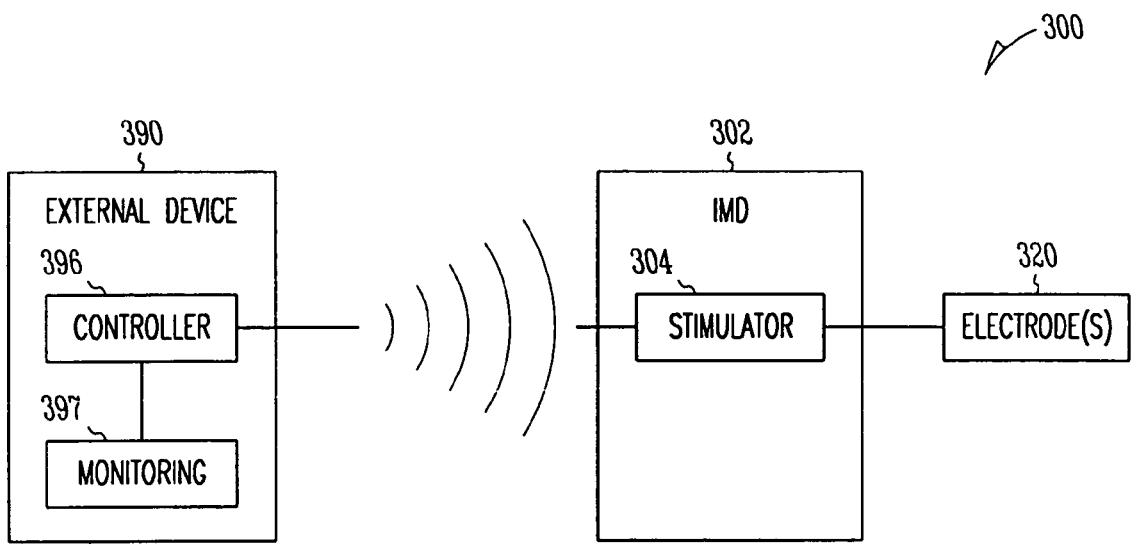
FIG. 3 illustrates a system for reducing proarrhythmic effects of neural stimulation including an external device, according to one embodiment.

FIG. 3 illustrates a system for reducing proarrhythmic effects of neural stimulation including an external device, according to one embodiment. The system 300 includes an implantable medical device 302 including a neural stimulator 304 adapted to deliver an electrical signal through at least one electrode 320 to provide vagal stimulation, including cardioprotective vagal stimulation in an embodiment. The system also includes an external monitoring device 390 wirelessly coupled to the stimulator. According to various embodiments, the external device 390 includes a monitoring module 397 adapted to monitor atrial activity to measure atrial vulnerability. The external device also includes a controller module 396 adapted to receive atrial arrhythmia vulnerability data from the monitoring module and to control the neural stimulator 304 to limit atrial proarrhythmia using the atrial arrhythmia vulnerability data, according to an embodiment. According to various embodiments, the external monitoring device includes a personal computer. The external monitoring device includes an advanced patient management (APM) system, according to an embodiment. According to various embodiments, the controller module is further adapted to receive atrial arrhythmic history data and to control the neural stimulator to limit atrial proarrhythmia using the atrial arrhythmic history data.

Figure 4:
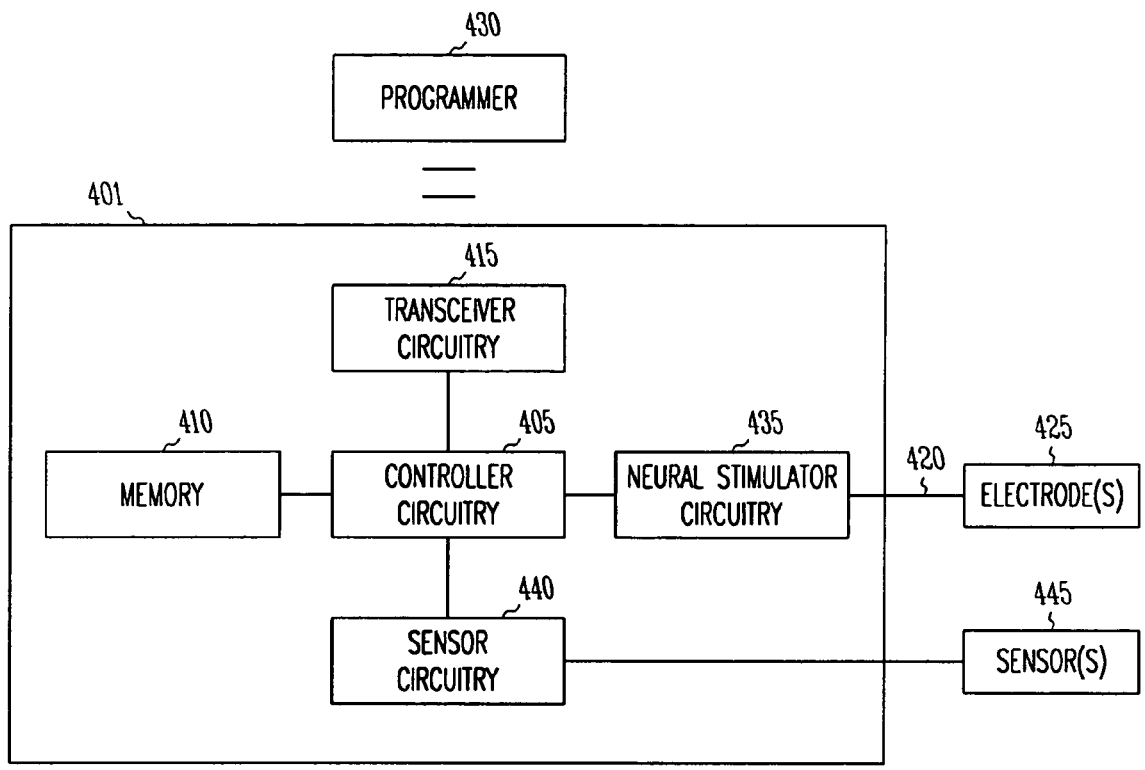
FIG. 4 is a schematic illustration of an implantable system for reducing proarrhythmic effects of neural stimulation, according to one embodiment.

FIG. 4 is a schematic illustration of an implantable system for reducing proarrhythmic effects of neural stimulation, according to one embodiment. The system includes an IMD 401, an electrical lead 420 coupled to the IMD 401, and at least one electrode 425. The IMD includes a controller circuit 405, a memory circuit 410, a telemetry circuit 415, and a neural stimulation circuit 435. The controller circuit 405 is operable on instructions stored in the memory circuit to deliver an electrical neural stimulation therapy. Therapy is delivered by the neural stimulation circuit 435 through the lead 420 and the electrode(s) 425. The telemetry circuit 415 allows communication with an external programmer 430. The programmer 430 can be used to adjust the programmed therapy provided by the IMD 401, and the IMD can report device data (such as battery and lead resistance) and therapy data (such as sense and stimulation data) to the programmer using radio telemetry, for example. According to various embodiments, the IMD 401 senses one or more physiological parameters and delivers neural stimulation therapy as disclosed in the method depicted in FIG. 6, described below. The illustrated system also includes sensor circuitry 440 that is coupled to at least one sensor 445. The controller circuit 405 processes sensor data from the sensor circuitry and delivers a therapy responsive to the sensor data.

Figure 5:
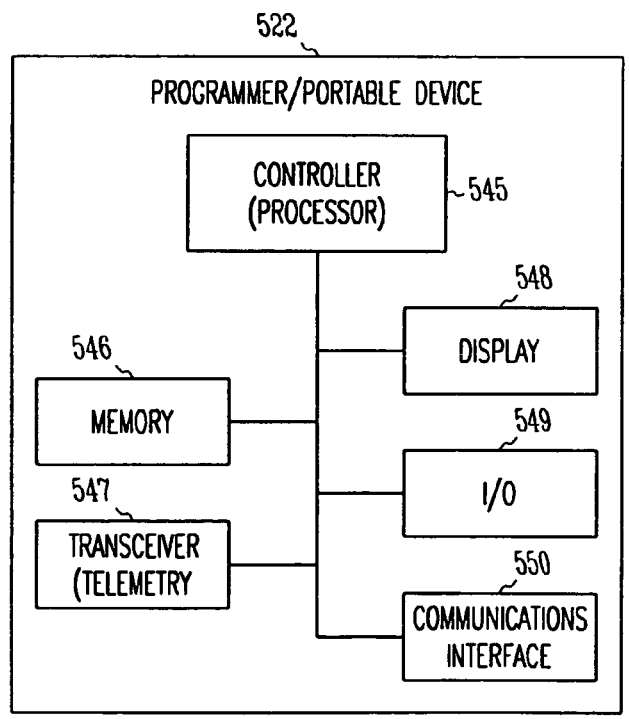
FIG. 5 illustrates a programmer such as illustrated in the system of FIG. 4 or other external device to communicate with the IMD(s), according to one embodiment.

FIG. 5 illustrates a programmer such as illustrated in the system of FIG. 4 or other external device to communicate with the IMD(s), according to one embodiment. An example of another external device includes Personal Digital Assistants (PDAs) or personal laptop and desktop computers in an Advanced Patient Management (APM) system. The illustrated device 522 includes controller circuitry 545 and a memory 546. The controller circuitry 545 is capable of being implemented using hardware, software, and combinations of hardware and software. For example, according to various embodiments, the controller circuitry 545 includes a processor to perform instructions embedded in the memory 546 to perform a number of functions, including communicating data and/or programming instructions to the implantable devices. The illustrated device 522 further includes a transceiver 547 and associated circuitry for use to communicate with an implantable device. Various embodiments have wireless communication capabilities. For example, various embodiments of the transceiver 547 and associated circuitry include a telemetry coil for use to wirelessly communicate with an implantable device. The illustrated device 522 further includes a display 548, input/output (I/O) devices 549 such as a keyboard or mouse/pointer, and a communications interface 550 for use to communicate with other devices, such as over a communication network.

Methods of Reducing Proarrhythmic Effects of Neural Stimulation

Figure 6:
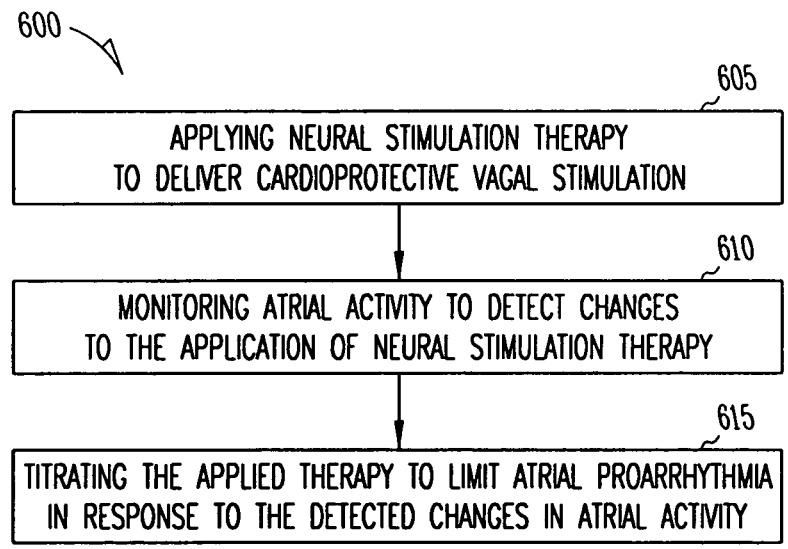
FIG. 6 illustrates a flow diagram of a method of titrating neural stimulation therapy to reduce proarrhythmic effects of neural stimulation, according to one embodiment.

FIG. 6 illustrates a flow diagram of a method of titrating neural stimulation therapy to reduce proarrhythmic effects of neural stimulation, according to one embodiment. The method 600 includes applying neural stimulation therapy to deliver vagal stimulation, including cardioprotective vagal stimulation in an embodiment, at 605. The method also includes monitoring atrial activity to detect changes related to the application of neural stimulation therapy, at 610. The method further includes titrating the applied therapy to limit atrial proarrhythmia in response to the detected changes in atrial activity, at 615. According to various embodiments, the method further includes receiving atrial arrhythmic history data and titrating the applied therapy to limit atrial proarrhythmia using the atrial arrhythmic history data.

According to various embodiments, monitoring atrial activity includes monitoring atrial arrhythmia frequency. Monitoring atrial activity includes monitoring atrial arrhythmia duration, according to an embodiment. In one embodiment, monitoring atrial activity includes monitoring atrial arrhythmia etiology. Monitoring atrial activity includes monitoring relative timing of atrial arrhythmia related to delivery of neural stimulation therapy, in an embodiment. For example, therapy delivery may be limited to a specific time period related to atrial arrhythmic risk, such as daytime-only or nighttime-only based on the patient's arrhythmia history obtained from a device logbook or external advanced patient monitoring system (APM).

As previously discussed, the present disclosure includes the use of sensors and sensor circuitry for monitoring atrial activity, according to various embodiments. In one embodiment, monitoring atrial activity includes monitoring atrial arrhythmia activity using implanted cardiac leads. Monitoring atrial activity includes monitoring atrial arrhythmia activity using subcutaneous wireless electrocardiogram (ECG) measurements, in various embodiments.

Figure 7:
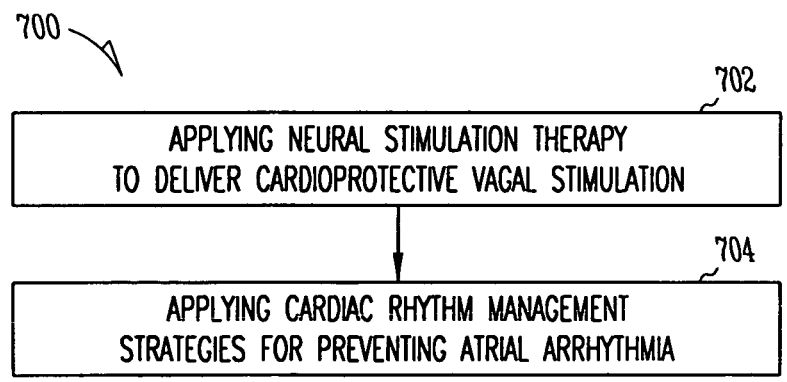
FIG. 7 illustrates a flow diagram of a method of applying atrial stimulation therapy to reduce proarrhythmic effects of neural stimulation, according to one embodiment.

FIG. 7 illustrates a flow diagram of a method of applying atrial stimulation therapy to reduce proarrhythmic effects of neural stimulation, according to one embodiment. The method 700 includes applying neural stimulation therapy to deliver vagal stimulation, including cardioprotective vagal stimulation in an embodiment, at 702. The method also includes applying cardiac rhythm management strategies for preventing atrial arrhythmia, at 704. According to various embodiments, the method further includes monitoring atrial activity to detect changes related to the application of neural stimulation therapy, and applying cardiac rhythm management strategies for preventing atrial arrhythmia in response to the detected changes in atrial activity. According to various embodiments, the method further includes receiving atrial arrhythmic history data and titrating the applied therapy to limit atrial proarrhythmia using the atrial arrhythmic history data.

According to various embodiments, applying cardiac rhythm management strategies includes applying atrial overdrive pacing. Applying cardiac rhythm management strategies includes applying atrial pacing preference, according to various embodiments. According to one embodiment, applying cardiac rhythm management strategies includes applying atrial anti-tachy pacing. Applying cardiac rhythm management strategies includes applying multi-site atrial pacing, according to an embodiment. According to various embodiments, applying cardiac rhythm management strategies includes automatically engaging algorithms for preventing paroxysmal atrial fibrillation. Applying cardiac rhythm management strategies includes applying atrial overdrive pacing if prior atrial tachycardia events have been detected, according to an embodiment.

One of ordinary skill in the art will understand that, the modules and other circuitry shown and described herein can be implemented using software, hardware, and combinations of software and hardware. As such, the illustrated modules and circuitry are intended to encompass software implementations, hardware implementations, and software and hardware implementations.

The methods illustrated in this disclosure are not intended to be exclusive of other methods within the scope of the present subject matter. Those of ordinary skill in the art will understand, upon reading and comprehending this disclosure, other methods within the scope of the present subject matter.

This application is intended to cover adaptations or variations of the present subject matter. It is to be understood that the above description is intended to be illustrative, and not restrictive. The scope of the present subject matter should be determined with reference to the appended claims, along with the full scope of equivalents to which such claims are entitled.

What is claimed is:

1. An implantable medical device, comprising:
    a sensor configured to sense atrial arrhythmia vulnerability data;
    a therapeutic stimulator configured to deliver an electrical signal to provide vagal stimulation; and
    means for controlling the therapeutic stimulator, the controlling means configured to receive sensed atrial arrhythmia vulnerability data and to control the therapeutic stimulator to reduce the vagal stimulation to limit atrial proarrhythmia using the sensed atrial arrhythmia vulnerability data,
    wherein the sensed atrial arrhythmia vulnerability data includes signs or symptoms of increased atrial vulnerability including at least one of: sensed changes in atrial arrhythmia etiology, relative timing of atrial arrhythmia related to the introduction or delivery of stimulation therapy; or sensed increases in premature atrial complexes (PACS), PAC trains or atrial flutter.

2. The device of claim 1, wherein the vagal stimulation includes cardioprotective vagal stimulation.

3. The device of claim 1, wherein the controlling means is further adapted to receive atrial arrhythmic history data and to control the therapeutic stimulator to limit atrial proarrhythmia using the atrial arrhythmic history data.

4. The device of claim 1, wherein the therapeutic stimulator includes a neural stimulator.

5. The device of claim 4, wherein the controlling means is adapted to control the neural stimulator to limit therapy delivery to a specific time period.

6. The device of claim 5, wherein the controlling means is adapted to control the neural stimulator to deliver therapy only when patient is awake.

7. The device of claim 5, wherein the controlling means is adapted to control the neural stimulator to deliver therapy only when patient is asleep.

8. The device of claim 1, wherein the therapeutic stimulator includes a cardiac stimulator adapted to provide cardiac rhythm management therapy.

9. The device of claim 4, wherein the controlling means is adapted to control the neural stimulator to reduce therapy delivery when one or more indicators of arrhythmic vulnerability are present.

10. The device of claim 9, wherein the one or more indicators of arrhythmic vulnerability include an increase in premature atrial complexes (PACs).

11. The device of claim 10, wherein the one or more indicators of arrhythmic vulnerability include an increase in PAC trains.

12. The device of claim 4, wherein the controlling means is adapted to control the neural stimulator to reduce therapy delivery based on atrial arrhythmic history data.

13. An implantable medical device, comprising:
    a sensor configured to sense atrial arrhythmia vulnerability data;
    a neural stimulator configured to deliver an electrical signal to provide vagal stimulation;
    a cardiac stimulator configured to deliver an electrical signal to provide cardiac rhythm management therapy; and
    a controller configured to receive sensed atrial arrhythmia vulnerability data and to control the neural stimulator to reduce the vagal stimulation and to control the cardiac stimulator to limit atrial proarrhythmia using the sensed atrial arrhythmia vulnerability data,
    wherein the sensed atrial arrhythmia vulnerability data includes signs or symptoms of increased atrial vulnerability including at least one of: sensed changes in atrial arrhythmia etiology, relative timing of atrial arrhythmia related to the introduction or delivery of stimulation therapy; or sensed increases in premature atrial complexes (PACS), PAC trains or atrial flutter.

14. The device of claim 13, wherein the vagal stimulation includes cardioprotective vagal stimulation.

15. The device of claim 13, wherein the controller is further adapted to receive atrial arrhythmic history data and to control the neural stimulator and the cardiac stimulator to limit atrial proarrhythmia using the atrial arrhythmic history data.

16. The device of claim 15, further comprising a memory adapted to be electrically connected to the controller, and wherein the controller is adapted to access atrial arrhythmic history data from the memory.

17. The device of claim 13, further comprising a sensor adapted to be electrically connected to the controller, and wherein the controller is adapted to receive atrial arrhythmia vulnerability data from the sensor.

18. An implantable medical device, comprising:
a neural stimulator configured to deliver an electrical signal to provide vagal stimulation;
at least one sensor configured to monitor atrial activity to measure atrial arrhythmia vulnerability;
a sensing circuit configured to be connected to the at least one sensor; and
a controller configured to receive measured atrial arrhythmia vulnerability data from the sensing circuit and to control the neural stimulator to reduce the vagal stimulation to limit atrial proarrhythmia using the measured atrial arrhythmia vulnerability data,
wherein the measured atrial arrhythmia vulnerability data includes signs or symptoms of increased atrial vulnerability including at least one of: sensed changes in atrial arrhythmia etiology, relative timing of atrial arrhythmia related to the introduction or delivery of stimulation therapy; or sensed increases in premature atrial complexes (PACS), PAC trains or atrial flutter.

19. The device of claim 18, wherein the vagal stimulation includes cardioprotective vagal stimulation.

20. The device of claim 18, wherein controller is further adapted to receive atrial arrhythmic history data and to control the neural stimulator to limit atrial proarrhythmia using the atrial arrhythmic history data.

21. The device of claim 18, wherein the at least one sensor is adapted to actively measure atrial electrophysiology parameters.

22. The device of claim 21, wherein the controller is adapted to control the neural stimulator to limit atrial proarrhythmia based on the atrial electrophysiology parameters.

23. The device of claim 21, wherein the atrial electrophysiology parameters include unipolar electrogram areas.

24. The device of claim 21, wherein the atrial electrophysiology parameters include atrial effective refractory periods (AERP).

25. A system, comprising:
at least one neural stimulation lead having a proximal portion and a distal portion;
a plurality of electrodes along the distal portion of the at least one lead; and
an implantable medical device coupled to the proximal portion of the at least one lead, the implantable device including:
a neural stimulator configured to deliver an electrical signal through at least one of the plurality of electrodes to provide cardioprotective vagal stimulation; and
a controller configured to receive atrial arrhythmia vulnerability data and to control the neural stimulator to reduce the vagal stimulation to limit atrial proarrhythmia using the atrial arrhythmia vulnerability data,
wherein the atrial arrhythmia vulnerability data includes signs or symptoms of increased atrial vulnerability including at least one of: sensed changes in atrial arrhythmia etiology, relative timing of atrial arrhythmia related to the introduction or delivery of stimulation therapy; or sensed increases in premature atrial complexes (PACS), PAC trains or atrial flutter.

26. The system of claim 25, wherein the at least one lead includes a transvascular lead.

27. The system of claim 25, wherein the implantable medical device includes a cardiac rhythm management device.

28. A system, comprising:
at least one electrode;
a neural stimulator configured to be implanted and further configured to deliver an electrical signal through the at least one electrode to provide cardioprotective vagal stimulation; and
an external monitoring device wirelessly coupled to the stimulator, the device including:
a monitoring module configured to monitor atrial activity to measure atrial vulnerability and produce atrial arrhythmia vulnerability data; and
a controller module configured to receive the atrial arrhythmia vulnerability data from the monitoring module and to control the neural stimulator to reduce the vagal stimulation to limit atrial proarrhythmia using the atrial arrhythmia vulnerability data,
wherein the atrial arrhythmia vulnerability data includes signs or symptoms of increased atrial vulnerability including at least one of: sensed changes in atrial arrhythmia etiology, relative timing of atrial arrhythmia related to the introduction or delivery of stimulation therapy; or sensed increases in premature atrial complexes (PACS), PAC trains or atrial flutter.

29. The system of claim 28, wherein the external monitoring device includes a personal computer.

30. The system of claim 28, wherein the external monitoring device includes an advanced patient management (APM) system.

* * * * *